United States Patent
Birke et al.

(10) Patent No.: US 6,921,752 B2
(45) Date of Patent: Jul. 26, 2005

(54) USE OF LTB4 ANTAGONISTS IN VETERINARY MEDICINE

(75) Inventors: Franz Birke, Ingelheim (DE); Kandace Matzek, Ingelheim (DE)

(73) Assignee: Boehringer Ingelheim Pharma GmbH & Co. KG, Ingelheim (DE)

(*) Notice: Subject to any disclaimer, the term of this patent is extended or adjusted under 35 U.S.C. 154(b) by 0 days.

(21) Appl. No.: 10/395,955

(22) Filed: Mar. 24, 2003

(65) Prior Publication Data

US 2003/0225004 A1 Dec. 4, 2003

Related U.S. Application Data

(60) Provisional application No. 60/385,147, filed on Jun. 3, 2002.

(30) Foreign Application Priority Data

Mar. 26, 2002 (DE) .......................... 102 13 350

(51) Int. Cl.$^7$ .................... A61K 31/70; A61K 31/7028; A61K 31/155
(52) U.S. Cl. .......................... 514/25; 514/637; 536/4.1; 564/244
(58) Field of Search .................... 514/25, 637; 536/4.1; 564/244

(56) References Cited

U.S. PATENT DOCUMENTS

| | | | |
|---|---|---|---|
| 5,246,965 A | 9/1993 | Main | |
| 5,366,982 A | * 11/1994 | Dereu et al. | 514/340 |
| 6,197,824 B1 | * 3/2001 | Schromm et al. | 514/637 |
| 6,265,612 B1 | 7/2001 | Schromm et al. | |
| 6,291,531 B1 | 9/2001 | Anderskewitz | |

FOREIGN PATENT DOCUMENTS

EP 0 544 488 A2 2/1993

OTHER PUBLICATIONS

Fink, Mitchell P. et al.: "A novel leukotriene B–4–receptor antagonist in endotoxin shock: A prospective, controlled trial in a porcine model." Critical Care Medicine, vol. 21, No. 12, 1993, pp. 1825–1837.

W.H.M. Stevens et al., "Effect of a Leukotriene B4 Receptor Antagonist SC–53228 on Ozone–Induced Airway Hyperresponsiveness and Inflamation in Dogs." Am. J. Resp. Crit. Care Med., vol. 152, pp. 1443–1448, 1995.

* cited by examiner

Primary Examiner—Elvis O. Price
Assistant Examiner—Michael C. Henry
(74) Attorney, Agent, or Firm—Michael P. Morris; Mary-Ellen M. Devlin; Alan R. Stempel

(57) ABSTRACT

The invention relates to the use of $LTB_4$ antagonists for preparing a pharmaceutical composition for the treatment or prevention of respiratory diseases in companion and domesticated animals.

5 Claims, No Drawings

USE OF LTB4 ANTAGONISTS IN VETERINARY MEDICINE

BACKGROUND TO THE INVENTION

The invention relates to the use of an $LTB_4$ antagonist or a prodrug thereof for preparing a pharmaceutical composition for the treatment or prevention of respiratory diseases in companion and domesticated animals.

$LTB_4$ antagonists are compounds with pharmacologically valuable properties. $LTB_4$ antagonists are used in human medicine for treating arthritis, asthma, chronic obstructive pulmonary disease, psoriasis, ulcerative colitis, Alzheimer's disease, shock, reperfusion damage/ischaemia, cystic fibrosis, atherosclerosis and multiple sclerosis.

$LTB_4$ antagonists are known, e.g., from International Patent Applications WO 93/16036, WO 94/11341, WO 96/02497, WO 97/21670, WO 98/11062, WO 98/11119, WO 01/25186, WO 01/51457 and WO 02/34715.

Diseases of the airways, particularly chronic diseases in companion and domesticated animals, generally have different causes from asthma or chronic obstructive pulmonary disease in humans. Because of these respiratory complaints, yields and performance will decrease sharply in domesticated or sporting animals, and thus lead to high economic losses. The medicaments used hitherto such as beta-mimetics or steroids lead to long waiting times in the case of animals bred for their meat and, in the case of animals used in sport, result in exclusion from competition on the grounds of suspicions of doping. In addition, some of these medicaments have limited efficacy and/or have undesirable side effects.

The problem of the present invention is therefore to provide a method of treating or preventing respiratory diseases in companion or domesticated animals, which treatment will lead to a rapid and lasting improvement in the health and performance of these animals without having the disadvantages of known treatment regimes.

SUMMARY OF THE INVENTION

It has now, surprisingly, been found that $LTB_4$ antagonists are exceptionally suitable for the treatment or prevention of respiratory diseases in such animals.

DETAILED DESCRIPTION OF THE INVENTION

The present invention relates to the use of an $LTB_4$ antagonist, or a prodrug thereof, for preparing a pharmaceutical composition for the treatment or prevention of respiratory diseases in companion and domesticated animals.

Preferred $LTB_4$ antagonists are those which have a benzamidine group of formula (1)

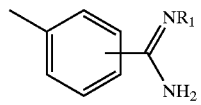

particularly compounds of formula I:

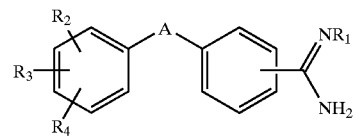

wherein

A denotes a group of formula

$$-O-C_mH_{2m}-O-(PHE)_n-$$ (II)

wherein
m is an integer from 2 to 6, preferably 2 to 5,
n is 0 or 1,
PHE denotes a 1,4-phenylene group optionally substituted by one or two $C_1$–$C_6$ alkyl groups, preferably a 1,4-phenylene group substituted by a $C_2$–$C_4$ alkyl group linked in the ortho position relative to the oxygen;

or

A denotes a group of formula

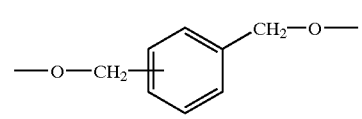

preferably of formula

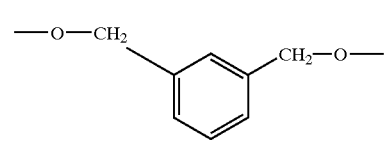

$R_1$ denotes H, OH, CN, $COR_{10}$, or CHO, preferably H or $COOR_{10}$;

$R_2$ denotes H, Br, Cl, F, $CF_3$, $CHF_2$, OH, $HSO_3$—O, $C_1$–$C_6$-alkyl, $C_1$–$C_6$-alkoxy, $C_5$–$C_7$-cycloalkyl, $CONR_8R_9$, aryl, O-aryl, $CH_2$-aryl, $CR_5R_6$-aryl, or $C(CH_3)_2$—$R_7$, preferably OH, $HSO_3$—O, $CONR_8R_9$ or $CR_5R_6$-aryl, $R_3$ denotes H, $C_1$–$C_6$-alkyl, $C_1$–$C_6$-alkoxy, OH, Cl or F, preferably H or $C_1$–$C_3$-alkoxy, $R_4$ denotes H or $C_1$–$C_6$-alkyl, preferably H;

$R_5$ denotes $C_1$–$C_4$-alkyl, $CF_3$, $CH_2OH$, COOH or COO($C_1$–$C_4$-alkyl), preferably $C_1$–$C_4$-alkyl, particularly methyl;

$R_6$ denotes H, $C_1$–$C_4$-alkyl or $CF_3$, preferably $C_1$–$C_4$-alkyl, particularly methyl;

$R_7$ denotes $CH_2OH$, COOH, COO($C_1$–$C_4$-alkyl), $CONR_8R_9$ or $CH_2NR_8R_9$;

$R_8$ denotes H, $C_1$–$C_6$-alkyl, phenyl, phenyl-($C_1$–$C_6$-alkyl), $COR_{10}$, $COOR_{10}$, CHO, $CONH_2$, $CONHR_{10}$, $SO_2$—($C_1$–$C_6$-alkyl), $SO_2$-phenyl, while the phenyl group may be mono- or disubstituted by Cl, F, $CF_3$, $C_1$–$C_4$-alkyl, OH and/or $C_1$–$C_4$-alkoxy, preferably $C_1$–$C_4$-alkyl, particularly isopropyl;

$R_9$ denotes H or $C_1$–$C_6$-alkyl, preferably H or $C_1$–$C_4$-alkyl, particularly isopropyl; or $R_8$ and $R_9$ together represent a $C_4$–$C_6$-alkylene group;

$R_{10}$ denotes $C_1$–$C_6$-alkyl, $C_5$–$C_7$-cycloalkyl, aryl, heteroaryl, aralkyl or heteroaryl-($C_1$–$C_6$-alkyl), preferably $C_1$–$C_4$-alkyl, while the aryl groups mentioned in groups $R_2$ and $R_{10}$ denote phenyl or naphthyl, the heteroaryl groups represent pyrrole, pyrazole, imidazole, furanyl, thienyl, pyridine or pyrimidine and may each be mono- or polysubstituted by Cl, F, $CF_3$, $C_1$–$C_4$-alkyl, OH, $HSO_3$—O or $C_1$–$C_4$-alkoxy, preferably by OH or $HSO_3$—O—, and, in the case of compounds substituted by OH, the corresponding glycosides thereof.

The invention further relates to pharmaceutical preparations containing at least one $LTB_4$ antagonist of formula I as well as at least one beta-mimetic or at least one steroid.

The invention further relates to a ready-to-use two-component system, wherein (a) one component contains at least one $LTB_4$ antagonist of formula I; and (b) the other component contains at least one beta-mimetic or at least one steroid.

Particularly preferred are $LTB_4$ antagonists of formula IA,

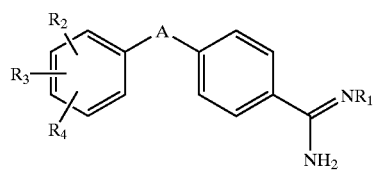

(IA)

wherein

A denotes a group of formula

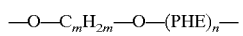

(II)

wherein m is an integer from 2 to 6, n is 0 or 1,

PHE denotes a 1,4-phenylene group substituted by a $C_1$–$C_6$ alkyl group;

or

A denotes a group of formula

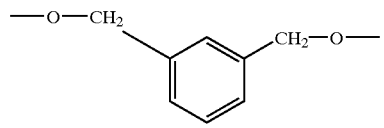

(IIIA)

$R_1$ denotes $COOR_{10}$;

$R_2$ denotes $CF_3$, $CHF_2$, OH, $HSO_3$—O, $C_1$–$C_6$-alkyl, $C_1$–$C_6$-alkoxy, $CONR_8R_9$ or $CR_5R_6$-aryl, $R_3$ denotes H or $C_1$–$C_6$-alkoxy, $R_4$ denotes H;

$R_5$ denotes $C_1$–$C_4$-alkyl;

$R_6$ denotes $C_1$–$C_4$-alkyl;

$R_8$ denotes H, $C_1$–$C_6$-alkyl, phenyl, phenyl-($C_1$–$C_6$-alkyl), $COR_{10}$, $COOR_{10}$, CHO, $CONH_2$, $CONHR_{10}$, $SO_2$—($C_1$–$C_6$-alkyl), $SO_2$-phenyl, while the phenyl group may be mono- or disubstituted by Cl, F, $CF_3$, $C_1$–$C_4$-alkyl, OH and/or $C_1$–$C_4$-alkoxy;

$R_9$ denotes H or $C_1$–$C_6$-alkyl; or $R_{10}$ denotes $C_1$–$C_6$-alkyl while the aryl groups mentioned in group $R_2$ denote phenyl and may each be monosubstituted by OH, $HSO_3$—O or $C_1$–$C_4$-alkoxy, and the pharmacologically acceptable acid addition salts thereof, the glycosides and O-sulphates thereof.

The active substance of formula I or IA may be present in the formulation according to the invention in the form of a physiologically acceptable acid addition salt. Examples of physiologically acceptable acid addition salts according to the invention are pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid. If desired, mixtures of the above acids may also be used to prepare the salts. According to the invention the salts of formula I selected from among the hydrochloride, hydrobromide, sulphate, phosphate, fumarate and methanesulphonate are preferred. Particularly preferred are the salts selected from among the hydrochloride, hydrobromide and fumarate. The active substance may optionally be present in the form of a hydrate. According to the invention, however, the compound of formula I is preferably added to the tablet in the form of the free base and in anhydrous form.

Particularly preferred compounds of formula I are those of formulae IA1 to IA8, particularly IA1:

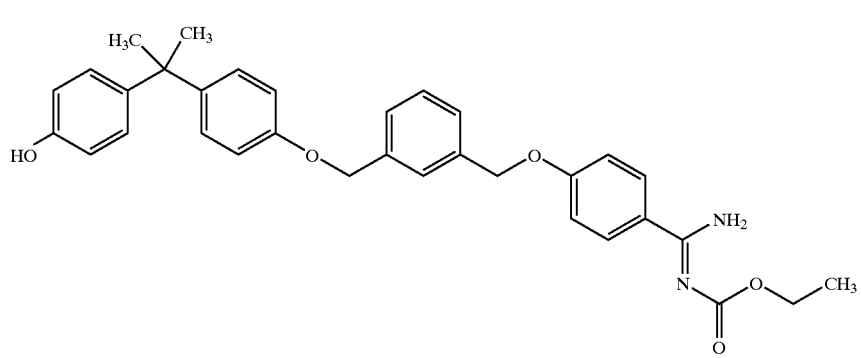

(IA1)

-continued
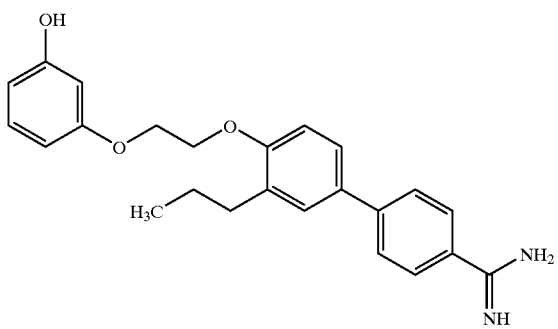
(IA2)
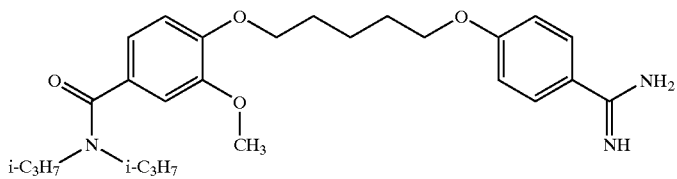
(IA3)
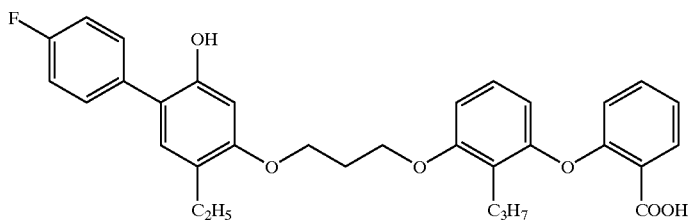
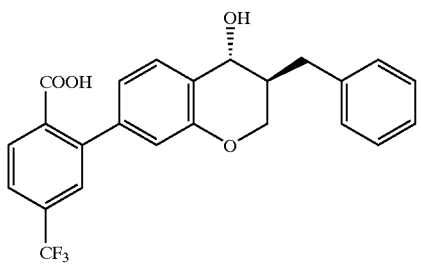
(IA4)
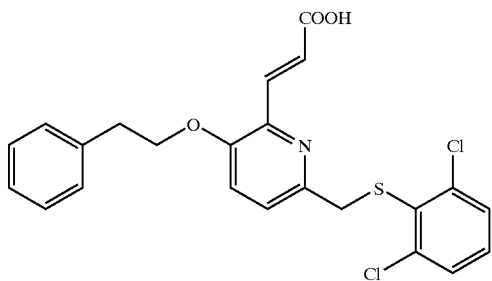
(IA5)
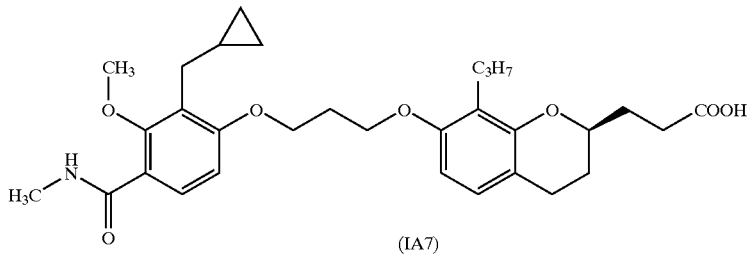
(IA6)
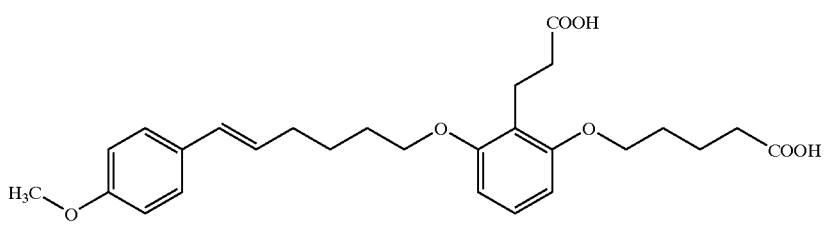
(IA7)
(IA8)

and, in the case of the compounds substituted by OH, the corresponding sulphates or glycosides thereof.

The compounds of formula I wherein $R_1$ is other than hydrogen are usually prodrugs which are converted in vivo into the corresponding compounds of formula I wherein $R_1$ is hydrogen.

From compound IA, for example, the compound of formula IA1:

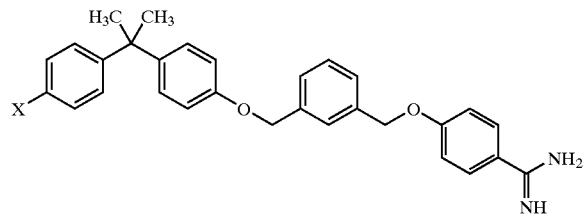

(IA1)

wherein X denotes OH, $HSO_3$—O or a carbohydrate group of formula $C_6H_{11}O_5$—O— is formed in vivo.

Preferably the active substance in each case is used in crystalline, unground or ground form, particularly in jet-ground form, with the particle size distribution being within the following limits: $D_{10} \leq 3$ μm, $D_{50}$ 3 to 8 μm, $D_{90} \leq 8$ to 30 μm. The numerical data given above for $D_{10}$, $D_{50}$ and $D_{90}$ in μm (microns) are the particle size ranges within which a total percentage of undersize particles of 10% by volume, 50% by volume or 90% by volume of the particles measured is obtained (cumulative volume distribution). These values were obtained by the laser diffractometry method, in this case particularly using a so-called dry dispersion under a dispersion pressure of 2 bar and a focal length f=500 mm, e.g. using a Sympatec/RODOS apparatus. This method is known in the art.

Where reference is made within the scope of the present invention to salts of the compounds of formula I, this is indicated by the symbol $\underline{I}'$. By contrast, explicit references to the free base of formula I are indicated by use of the symbol $\underline{I}$.

The phrase "companion animals" generally denotes animals kept for social reasons, particularly for leisure pursuits, such as and dogs and cats, and also horses kept for riding or sport.

The phrase "domesticated animals" generally denotes animals kept for economic purposes, for the production of food or wool or as working animals, especially for agricultural purposes. These are predominantly cloven-hoofed mammals, such as for example cattle, sheep and goats or pigs.

The active substance in question is generally administered orally, preferably in the form of a tablet, granules, suspension or as a feed additive.

Based on the total mass of the preparation, the $LTB_4$ antagonist according to the invention, preferably the compound of formula I, particularly IA, is present in an amount of from about 0.2 to about 95% by weight, preferably about 0.7 to about 60% by weight, more preferably about 5 to about 50% by weight. Most preferably, the proportion of the free base of $\underline{I}$ is between about 6 and about 40% by weight based on the total mass of the preparation.

The pharmaceutical formulation according to the invention also contains in addition to the active substance at least one excipient as a filler/dry binder.

Within the scope of the present invention, carbohydrates such as lactose or mannose, particularly finely divided lactose or sugar alcohols such as mannitol, sorbitol or xylitol, particularly mannitol, are particularly important as excipients. These excipients have proved particularly advantageous in the formulation according to the invention. According to a preferred aspect, the present invention therefore relates to a tablet containing at least one compound of formula I, which contains, in addition to the active substance and the wetting agent, lactose, particularly finely divided lactose, most preferably lactose monohydrate or mannitol as excipient.

The formulation according to the invention may also contain further excipients or fillers in addition to lactose, a wetting agent and the active substance. According to the invention it is preferable to use those compounds which are capable of acting as binders.

The term "binders" used above and hereinafter denotes those adjuvants which are capable of binding other components to one another. Preferred binders according to the invention are selected from the group consisting of: powdered cellulose, microcrystalline cellulose, sorbitol, starch, polyvinylpyrrolidone (povidone), copolymers of vinylpyrrolidone with other vinyl derivatives (copovidone), cellulose derivatives, particularly methylhydroxypropylcellulose, e.g. methocel A 15 LV, and mixtures of these compounds. Preferably, powdered cellulose and especially microcrystalline cellulose and/or copovidone are used as binders. Most preferable is a mixture of microcrystalline cellulose and a copolymer of vinylpyrrolidone and vinyl acetate, namely copovidone VA 64, where the ratio of vinylpyrrolidone to vinyl acetate is about 3:2 (m/m). As a rule the tablet according to the invention has a weight ratio of microcrystalline cellulose to copovidone VA 64 of about 20:1 to about 1:1, preferably about 15:1 to about 2:1, particularly about 10:1 to about 3:1. Because of this particularly preferred binder combination of microcrystalline cellulose and copovidone, tablets are obtained with increased bioavailability of the compounds of formula I.

The preparation according to the invention may also contain as additional ingredients flow or flow regulating agents as well as lubricants. These include, for example, within the scope of the present invention, silicon dioxide, talc, stearic acid, sodium stearylfumarate, magnesium stearate and glycerol tribehenate. According to the invention magnesium stearate is preferably used. If the flow or flow regulating agents or lubricants mentioned above are used, the amount by weight based on the total mass of the tablet according to the invention is preferably in the range from about 0.1–about 10% by weight, preferably about 0.5–about 5% by weight, more preferably between about 0.6 and about 1.5% by weight.

Furthermore, the formulation according to the invention may contain one or more synthetic or natural, pharmaceutically acceptable colourings, preferably indigo or carmine. If such colourings are used the amount by weight based on the total mass of the tablet according to the invention is about 0.01 to about 0.5% by weight.

In addition, the formulation according to the invention may contain one or more synthetic or natural, pharmaceutically acceptable odoriferous substances or flavourings. The nature of these odoriferous substances and flavourings will depend on the species of animal to be treated. If the abovementioned odoriferous substances or flavourings are used, the amount by weight based on the total mass of the tablet according to the invention would be about 0.01 to about 0.5% by weight.

The formulation of the invention may be prepared by mixing the ingredients directly, followed by compression and pelleting, or by granulation, compression and pelleting.

As a rule the $LTB_4$ antagonist is administered daily, e.g., combined with the animal's feed, at a dosage range of about 0.1 to about 20 mg/kg, preferably from about 0.5 to about 8.0 mg/kg.

The following Example serves to illustrate a use according to the invention. It should be understood as being merely an example of a possible procedure, without restricting the invention to its contents.

EXAMPLE

Description of the experiment conducted:

A horse (12 year old crossbred mare) has the following symptoms caused by chronic bronchitis: cough, shortness of breath, lethargy.

This horse is given 10 g of the compound of formula IA1 in the form of a methylcellulose (thylose) suspension with its feed (oats) once a day for 20 days.

After about seven (7) days' treatment there is a significant improvement in the symptoms: reduced coughing with a spell of several days without coughing, improved performance (exercise capacity), vitality and agility. The earlier symptoms returned about two (2) weeks after the treatment.

The $LTB_4$ antagonist of formula IA1 was well tolerated with no signs of any side effects.

What is claimed is:

1. A method for treating chronic bronchitis in a horse, which method comprises administering to the affected horse a therapeutically effective amount of a $LTB_4$ antagonist, wherein the $LTB_4$ antagonist is a compound of formula I,

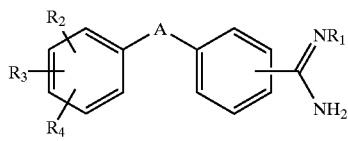
(I)

wherein
A denotes a group of formula

(II)

wherein
m is an integer from 2 to 6,
n is 0 or 1,
PHE denotes a 1,4-phenylene group optionally substituted by one or two $C_1$–$C_8$ alkyl groups;
or
A denotes a group of formula

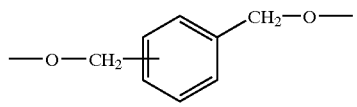
(III)

$R_1$ denotes H, OH, CN, $COR_{10}$, $COOR_{10}$ or CHO;
$R_2$ denotes H, Br, Cl, F, $CF_3$, $CHF_2$, OH, $HSO_3$—O, $C_1$–$C_6$-alkyl, $C_1$–$C_6$-alkoxy, $C_5$–$C_7$-cycloalkyl, $CONR_8R_9$, aryl, O-aryl, $CH_2$-aryl, $CR_5R_6$-aryl, or $C(CH_3)_2$—$R_7$;
$R_3$ denotes H, $C_1$–$C_6$-alkyl, $C_1$–$C_6$-alkoxy, OH, Cl or F,
$R_4$ denotes H or $C_1$–$C_6$-alkyl;
$R_5$ denotes $C_1$–$C_4$-alkyl, $CF_3$, $CH_2OH$, COOH or COO($C_1$–$C_4$-alkyl);
$R_6$ denotes H, $C_1$–$C_4$-alkyl or $CF_3$;
$R_7$ denotes $CH_2OH$, COOH, COO($C_1$–$C_4$-alkyl), $CONR_8R_9$ or $CH_2NR_8R_9$;
$R_8$ denotes H, $C_1$–$C_6$-alkyl, phenyl, phenyl-($C_1$–$C_6$-alkyl), $COR_{10}$, $COOR_{10}$, CHO, $CONH_2$, $CONHR_{10}$, $SO_2$—($C_1$–$C_6$-alkyl), $SO_2$-phenyl, while the phenyl group may be mono- or disubstituted by Cl, F, $CF_3$, $C_1$–$C_4$-alkyl, OH and/or $C_1$–$C_4$-alkoxy;

$R_9$ denotes H or $C_1$–$C_6$-alkyl; or
$R_8$ and $R_9$ together represent a $C_4$–$C_6$-alkylene group;
$R_{10}$ denotes $C_1$–$C_6$-alkyl, $C_5$–$C_7$-cycloalkyl, aryl, heteroaryl, aralkyl or heteroaryl-($C_1$–$C_6$-alkyl),
while the aryl groups mentioned in groups $R_2$ and $R_{10}$ denote phenyl or naphthyl, the heteroaryl groups denote pyrrole, pyrazote, imidazole, furanyl, thienyl, pyridine or pynmidine and may each be mono- or polysubstituted by Cl, F, $CF_3$, $C_1$–$C_4$-alkyl, OH, $HSO_3$—O or $C_1$–$C_4$-alkoxy,
and the pharmacologically acceptable acid addition salts thereof, the glycosides and O-sulphates thereof.

2. The method as recited in claim 1, wherein the $LTB_4$ antagonist is a compound of formula IA,

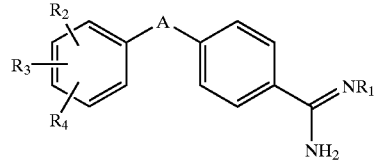
(IA)

wherein
A denotes a group of formula

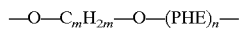
(II)

wherein
m is an integer from 2 to 6,
n is 0 or 1,
PHE denotes a 1,4-phenylene group substituted by a $C_1$–$C_6$ alkyl group;
or
A denotes a group of formula

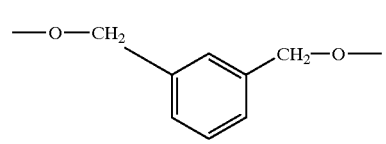
(IIIA)

$R_1$ denotes $COOR_{10}$;
$R_2$ denotes $CF_3$, $CHF_2$, OH, $HSO_3$—O, $C_1$–$C_6$-alkyl, $C_1$–$C_6$-alkoxy, $CONR_8R_9$ or $CR_5R_6$-aryl,
$R_3$ denotes H or $C_1$–$C_6$-alkoxy,
$R_4$ denotes H;
$R_5$ denotes $C_1$–$C_4$-alkyl;
$R_6$ denotes $C_1$–$C_4$-alkyl;
$R_8$ denotes H, $C_1$–$C_6$-alkyl, phenyl, phenyl-($C_1$–$C_6$-alkyl), $COR_{10}$, $COOR_{10}$, CHO, $CONH_2$, $CONHR_{10}$, $SO_2$—($C_1$–$C_6$-alkyl), $SO_2$-phenyl, while the phenyl group may be mono- or disubstituted by Cl, F, $CF_3$, $C_1$–$C_4$-alkyl, OH and/or $C_1$–$C_4$-alkoxy;
$R_9$ denotes H or $C_1$–$C_6$-alkyl; or
$R_{10}$ denotes $C_1$–$C_6$-alkyl,
while the aryl groups mentioned in the group $R_2$ denote phenyl and may each be monosubstituted by OH, $HSO_3$—O or $C_1$–$C_4$-alkoxy,
and the pharmacologically acceptable acid addition salts thereof, the glycosides and O-suiphates thereof.

3. A method for treating chronic bronchitis in a horse, which method comprises administering to the affected horse a therapeutically effective amount of a $LTB_4$ antagonist, wherein the $LTB_4$ antagonist is a compound selected from formulae IA1 to IA8:

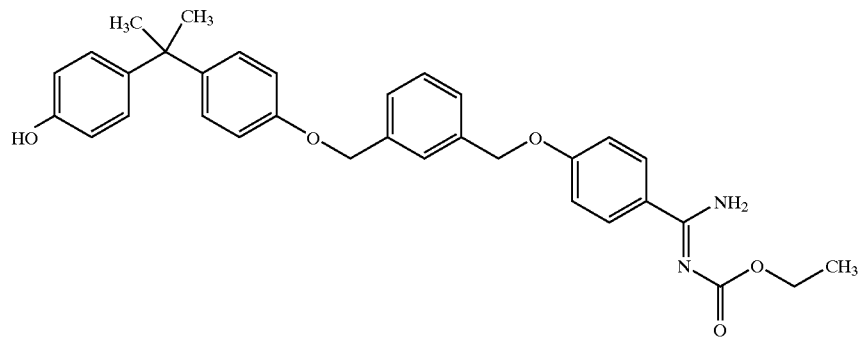
(IA1)
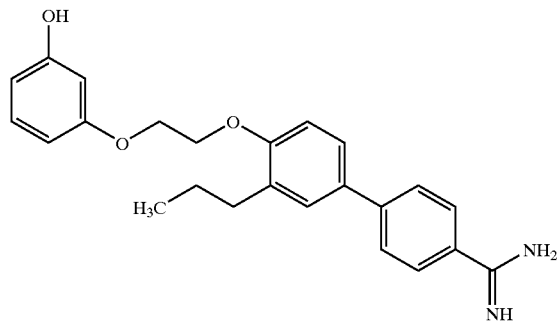
(IA2)
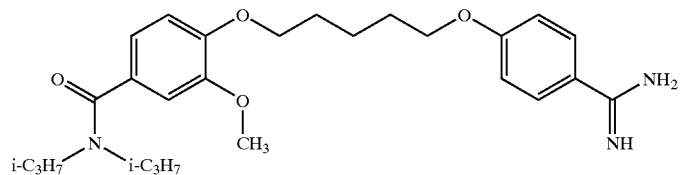
(IA3)
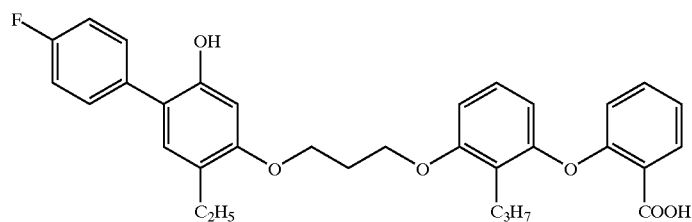
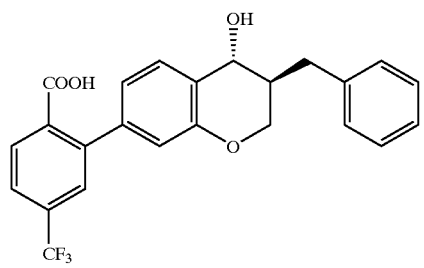
(IA4)
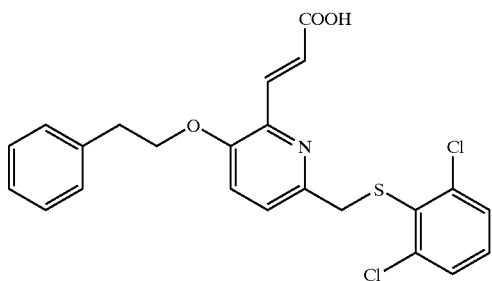
(IA5)

-continued

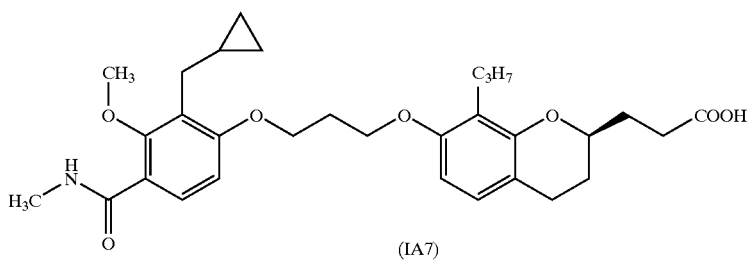
(IA6)

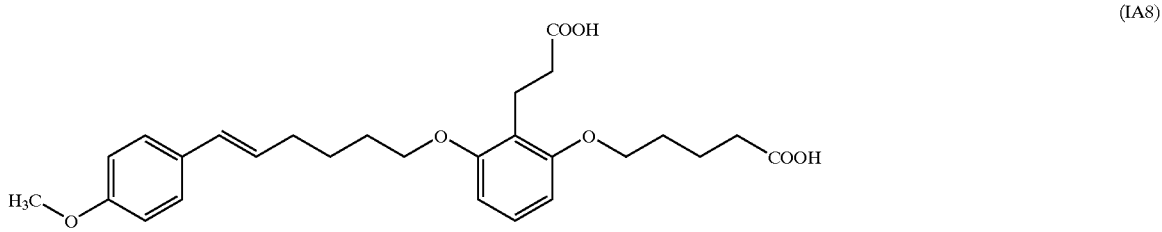
(IA7)

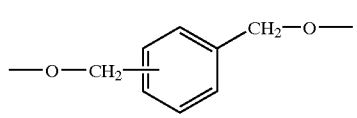
(IA8)

and, in the case of compounds substituted by OH, the corresponding sulphates or glycosides thereof.

4. A method for preventing chronic bronchitis in a horse which comprises administering to the horse a prophylactic amount of a $LTB_4$ antagonist compound of formula I

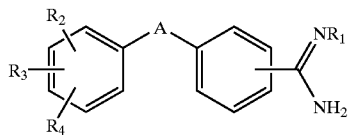
(I)

wherein
A denotes a group of formula

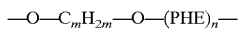
(II)

wherein
m is an integer from 2 to 6,
n is 0 or 1,
PHE denotes a 1,4-phenylene group optionally substituted
by one or two $C_1$–$C_6$ alkyl groups;
or
A denotes a group of formula —O—CH$_2$—[phenyl]—CH$_2$—O— (III)

$R_1$ denotes H, OH, CN, $COR_{10}$, $COOR_{10}$ or CHO;
$R_2$ denotes H, Br, Cl, F, $CF_3$, $CHF_2$, OH, $HSO_3$—O, $C_1$–$C_6$-alkyl, $C_1$–$C_6$-alkoxy, $C_5$–$C_7$-cycloalkyl, $CONR_8R_9$, aryl, O-aryl, $CH_2$-aryl, $CR_5R_6$-aryl, or $C(CH_3)_2$—$R_7$, $R_3$ denotes H, $C_1$–$C_6$-alkyl, $C_1$–$C_6$-alkoxy, OH, Cl or F, $R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl or $CF_3$;

$R_7$ denotes $CH_2OH$, COOH, COO($C_1$–$C_4$-alkyl), $CONR_8R_9$ or $CH_2NR_8R_9$;

$R_8$ denotes H, $C_1$–$C_6$-alkyl, phenyl, phenyl-($C_1$–$C_6$-alkyl), $COR_{10}$, $COOR_{10}$, CHO, $CONH_2$, $CONHR_{10}$, $SO_2$—($C_1$–$C_6$-alkyl), $SO_2$-phenyl, while the phenyl group may be mono- or disubstituted by Cl, F, $CF_3$, $C_1$–$C_4$-alkyl, OH and/or $C_1$–$C_4$-alkoxy;

$R_9$ denotes H or $C_1$–$C_8$-alkyl; or $R_8$ and $R_9$ together represent a $C_4$–$C_6$-alkylene group;

$R_{10}$ denotes $C_1$–$C_6$-alkyl, $C_5$–$C_7$-cycloalkyl, aryl, heteroaryl, aralkyl or heteroaryl-($C_1$–$C_6$-alkyl), while the aryl groups mentioned in groups $R_2$ and $R_{10}$ denote phenyl or naphthyl, the heteroaryl groups denote pyrrole, pyrazole, imidazole, furanyl, thienyl, pyridine or pyrimidine and may each be mono- or polysubstituted by Cl, F, $CF_3$, $C_1$–$C_4$-alkyl, OH, $HSO_3$—O or $C_1$–$C_4$-alkoxy, and the pharmacologically acceptable acid addition salts thereof, the glycosides and O-sulphates thereof.

5. A method for preventing chronic bronchitis in a horse, which method comprises administering to the affected horse a therapeutically effective amount of a $LTB_4$ antagonist, wherein the $LTB_4$ antagonist is a compound selected from formulae IA1 to IA8:

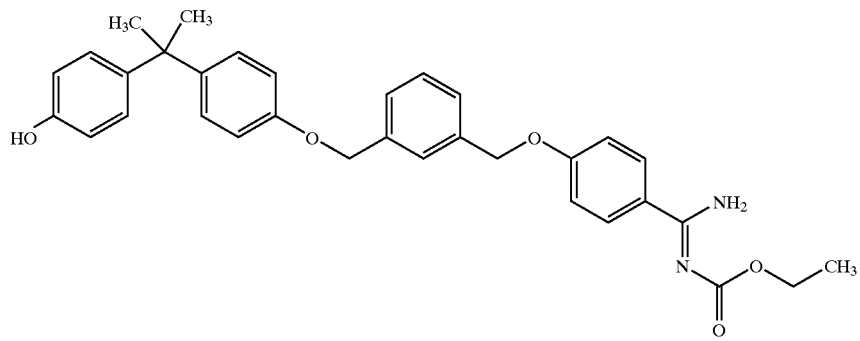
(IA1)
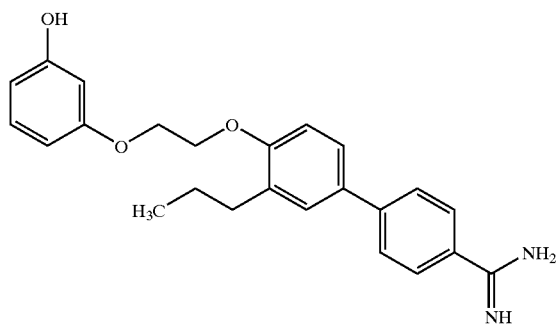
(IA2)
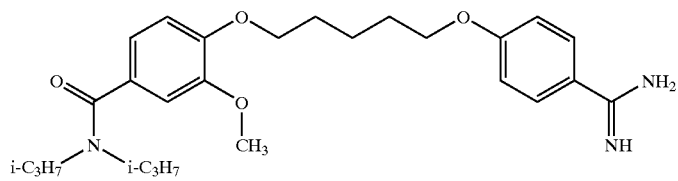
(IA3)
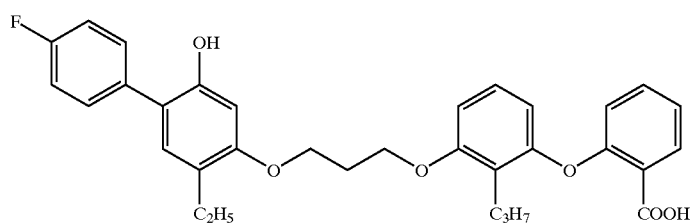
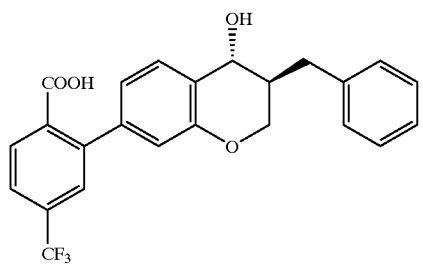
(IA4)
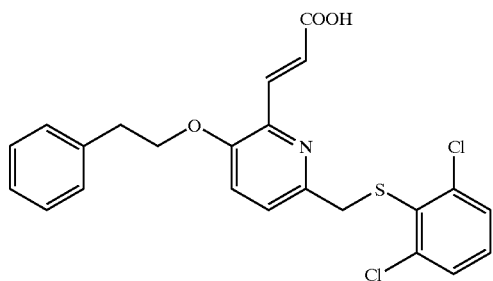
(IA5)

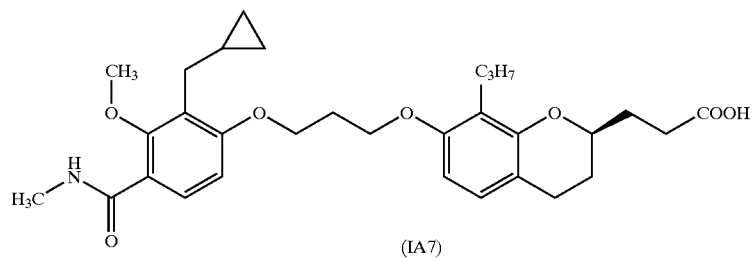
(IA7)
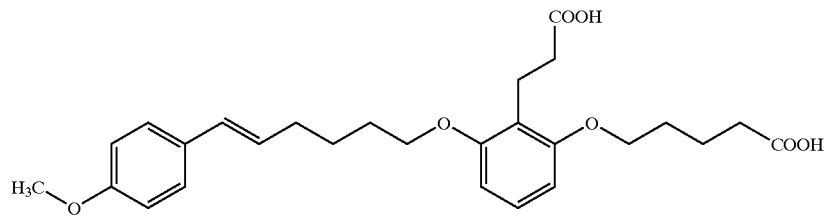
(IA8)
and, in the case of compounds substituted by OH, the corresponding sulphates or glycosides thereof.